US006991761B2

(12) United States Patent
Hehenberger et al.

(10) Patent No.: US 6,991,761 B2
(45) Date of Patent: Jan. 31, 2006

(54) INFORMATION MANAGEMENT AND MATERIAL DISTRIBUTION FOR STERILIZATION FACILITIES

(75) Inventors: Rodney K. Hehenberger, Apple Valley, MN (US); Terry S. Nees, Shoreview, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 678 days.

(21) Appl. No.: 10/029,355

(22) Filed: Oct. 26, 2001

(65) Prior Publication Data

US 2003/0083902 A1  May 1, 2003

(51) Int. Cl.
*G06F 17/30*  (2006.01)
(52) U.S. Cl. .................. 422/3; 705/2; 705/28; 707/1; 707/10
(58) Field of Classification Search .................. 705/2, 705/28, 1; 422/105, 119; 707/1, 10
See application file for complete search history.

(56) References Cited

U.S. PATENT DOCUMENTS

| | | | |
|---|---|---|---|
| 5,193,065 A * | 3/1993 | Guerindon et al. ......... 700/106 |
| 5,610,811 A | 3/1997 | Honda | |
| 5,671,362 A | 9/1997 | Cowe et al. | |
| 5,671,363 A | 9/1997 | Cristofich et al. | |
| 5,748,907 A | 5/1998 | Crane | |
| 5,752,234 A | 5/1998 | Withers | |
| 5,893,070 A | 4/1999 | Garber et al. | |
| 5,930,771 A | 7/1999 | Stapp | |
| 5,974,388 A | 10/1999 | Durham | |
| 5,991,728 A | 11/1999 | DeBusk et al. | |
| 5,996,889 A | 12/1999 | Fuchs et al. | |
| 6,021,392 A | 2/2000 | Lester et al. | |
| 6,023,683 A | 2/2000 | Johnson et al. | |
| 6,112,182 A | 8/2000 | Akers et al. | |
| 6,148,297 A * | 11/2000 | Swor et al. ..................... 707/3 |
| 6,223,137 B1 | 4/2001 | McCay et al. | |
| 6,485,979 B1 * | 11/2002 | Kippenhan et al. ............ 436/1 |
| 6,578,002 B1 * | 6/2003 | Derzay et al. ................. 705/2 |
| 6,628,777 B1 * | 9/2003 | McIllwaine et al. ... 379/265.01 |

(Continued)

FOREIGN PATENT DOCUMENTS

EP        0 630 820 A1   12/1994

(Continued)

OTHER PUBLICATIONS

3M Record Keeping Software 1213A, User's Guide, Version 1.0, 2001.

*Primary Examiner*—John Kim
*Assistant Examiner*—Brad Y. Chin
(74) *Attorney, Agent, or Firm*—Shumaker & Sieffert, P.A.

(57) ABSTRACT

An automated system for management of information and distribution of materials associated with sterilization procedures includes a network server and client computers that communicate via a computer network. The client computers are distributed among sterilization facilities that require sterilization services. The network server exchanges a variety of information with the sterilization facilities. In response to information from client computers, the network server may trigger distribution of materials to sterilization facilities, and generates reports for record-keeping or cost-accounting purposes. The information distributed by the network server may pertain to the operation, maintenance and control of sterilization equipment, characteristics and capabilities of sterilization materials, and expert technical advice. The information received from sterilization facilities includes requests for information, orders for purchase and delivery of materials, and sterilization process information documenting sterilization procedures performed within a sterilization facility.

14 Claims, 5 Drawing Sheets

U.S. PATENT DOCUMENTS

| | | | |
|---|---|---|---|
| 2002/0055853 A1 * | 5/2002 | Macleod Beck et al. | 705/1 |
| 2002/0119074 A1 * | 8/2002 | McGowan, Jr. | 422/26 |
| 2002/0147502 A1 * | 10/2002 | Price et al. | 700/1 |
| 2002/0169514 A1 * | 11/2002 | Eryurek et al. | 700/110 |
| 2002/0194014 A1 * | 12/2002 | Stames et al. | 705/1 |
| 2003/0055666 A1 * | 3/2003 | Roddy et al. | 705/1 |
| 2003/0078805 A1 * | 4/2003 | Ng et al. | 705/2 |
| 2004/0098159 A1 * | 5/2004 | Brown | 700/117 |

FOREIGN PATENT DOCUMENTS

| | | |
|---|---|---|
| JP | 2000-107994 | 4/2000 |
| WO | WO 99/66444 | 12/1999 |
| WO | WO 01/10476 | 2/2001 |

* cited by examiner

INFORMATION MANAGEMENT AND MATERIAL DISTRIBUTION FOR STERILIZATION FACILITIES

TECHNICAL FIELD

The invention relates to the health care industry and, more particularly, to administration of sterilization procedures in a health care facility.

BACKGROUND

In a health care facility, sterilization generally refers to the process of eliminating bacteria and other microorganisms from the surfaces of instruments, medical devices, implants and other articles used in surgical procedures. A traditional sterilization process uses steam under pressure. Alternative sterilization processes use ethylene oxide, hydrogen peroxide, hydrogen peroxide/plasma, or peracetic acid in vapor form as the sterilant, as well as gamma irradiation and electron beam sterilization. In each process, the sterilizer is designed to kill all viable living organisms within a sterilization chamber. To achieve this objective, health care personnel must select the appropriate sterilization process and carefully monitor its parameters.

To verify successful sterilization, health care facilities typically use sterilization indicators of either the chemical or biological variety. A chemical sterilization indicator responds to one or more conditions necessary for proper sterilization, such as temperature, time, and sterilant concentration or exposure. A biological indicator carries a biological agent, and indicates successful sterilization when the biological agent has been killed. The indicator is placed on or within a pack containing articles to be sterilized.

Following the sterilization process, the sterilization indicator aids health care personnel in identifying packs that have been exposed to the conditions necessary for sterilization. The pack may carry other information, often within the indicator, that identifies the pack for record-keeping purposes. For example, the indicator may carry text or bar code information that uniquely identifies the pack, and indicates sterilization status. In some cases, the information can be scanned in an automated manner to assist in automated record-keeping via a computer system.

To achieve effective sterilization workflow, record-keeping, and safety, a health care facility must devote substantial personnel, training and administrative resources to the sterilization process. For example, it is necessary to maintain a sufficient inventory of sterilant, pack lists, and indicators, and properly maintain sterilization equipment. Comprehensive knowledge of sterilization procedures and control of associated parameters are necessary for proper sterilization. In addition, efficient workflow requires effective tracking of packs to ensure that sterilized articles are available when needed. Cost accounting also is desirable to allocate the costs of sterilization to appropriate departments or entities. In addition, regulatory agencies and independent audit organizations may require access to sterilization records for verification of regulatory compliance or accreditation. Access to information concerning best practices also is important in maintaining and refining sterilization processes within a sterilization facility.

SUMMARY

In general, the invention is directed to an automated system for management of information and distribution of materials associated with sterilization procedures. The invention may be implemented via a computer network having at least one network server and client computers distributed among a number of sterilization facilities. In particular, the network server exchanges information with sterilization facilities via the client computers. For example, the network server may provide the sterilization facilities with information relating to sterilization products or processes. In response to information received from the sterilization facilities, the network server may trigger distribution of sterilization materials to the sterilization facilities, and generate reports for record-keeping or cost-accounting purposes.

The information distributed by the network server may include information pertaining to the operation, maintenance and control of sterilization equipment and processes, the characteristics and capabilities of commercially available sterilization materials such as particular sterilants, pack lists, and indicators, and expert advice delivered in real-time, e.g., via an online chat room facility, or by email or other communication media. The information received from the sterilization facilities may include requests for information, orders for purchase and shipment of materials, and cost accounting and record-keeping information pertaining to the sterilization procedures performed by the sterilization facilities in the course of their operations.

The network server may trigger the distribution of materials by communicating orders to automated product ordering systems or individuals responsible for order fulfillment. The network server may trigger distribution of materials based on direct requests communicated from sterilization facilities. Alternatively, the network server may be equipped to monitor sterilization process information communicated by the sterilization facilities to determine when a need for additional materials exits. In this case, the network server delivers materials on a predictive basis to maintain sterilization product inventory and keep the operations of a sterilization facility running smoothly.

The materials distributed according to requests generated by the network server may include consumable materials such as sterilants, pack lists, and indicators, as well as software executed by sterilization facility computers to prepare and process indicators. For example, a sterilization facility may provide the network server with information concerning consumption of sterilants, pack lists, indicators and the like, either directly or as part of other information pertaining to sterilization processes within the sterilization facility. In addition, a client computer may directly request the download of software that, for example, drives the printing of identification codes, such as bar codes, on a pack or indicator, defines an indicator image to be printed, or prints a pack list for central service employees. In some cases, the identification code may be printed with self-indicating ink, i.e., ink that changes appearance to indicate the sterilization status of a pack.

In addition, the network server can be configured to generate reports based on information communicated by the sterilization facilities. For example, a client interface can be incorporated in the sterilization facility to permit communication of sterilization process monitoring information to the network server. The sterilization process monitoring information may indicate the status of sterilization equipment, sterilization loads and particular packs within a load. On this basis, the network server can generate reports, for real-time access or archival, that track operations within a sterilization facility. In some cases, the reports can be made accessible by the sterilization facilities as well as regulatory agencies or independent audit organizations to verify compliance with applicable standards. In other cases, the reports may contain cost-accounting information for the chargeback of sterilization costs to particular departments within a health care facility.

In one embodiment, the invention provides a method comprising receiving sterilization process information from a sterilization facility via a computer network, generating a report based on the received information, and providing a network client with access to the report via the computer network.

In another embodiment, the invention provides a system comprising a client computer and a network server. The client computer, associated with a sterilization facility, transmits sterilization process information via a computer network. The network server receives the sterilization process information from the client computer via the computer network, generates a report based on the received information, and provides a network client with access to the report via the computer network.

In an added embodiment, the invention provides a method comprising receiving sterilization process information from a sterilization facility via a computer network, determining consumption of a quantity of a sterilization material by the sterilization facility based on the sterilization process information, and processing an order for delivery of an additional quantity of the sterilization material to the sterilization facility based on the determination.

In a further embodiment, the invention provides a system comprising a client computer associated with a sterilization facility. The client computer transmits sterilization process information via a computer network to a network server. The network server determines consumption of a quantity of a sterilization material by the sterilization facility based on the sterilization process information, and processes an order for delivery of an additional quantity of the sterilization material to the sterilization facility based on the determination.

In another embodiment, the invention provides a method comprising receiving sterilization process information from a sterilization facility via a computer network. The method further comprises determining consumption of a quantity of a sterilization material by the sterilization facility based on the sterilization process information, and processes an order for delivery of an additional quantity of the sterilization material to the sterilization facility based on the determination. In addition, the method involves scheduling maintenance for sterilization equipment associated with the sterilization facility based on the sterilization process information, and generating a report that indicates compliance with sterilization process standards based on the sterilization process information. A network client may be given access to the report via the computer network.

In an added embodiment, the invention provides a system comprising a client computer, associated with a sterilization facility, that transmits sterilization process information via a computer network to a network server. The network server determines consumption of a quantity of a sterilization material by the sterilization facility based on the sterilization process information, and processes an order for delivery of an additional quantity of the sterilization material to the sterilization facility based on the determination. The network server also schedules maintenance for sterilization equipment associated with the sterilization facility based on the sterilization process information. Further, the network server generates a report that indicates compliance with sterilization process standards based on the sterilization process information, and provides a reviewer with access to the report via the computer network.

In another embodiment, the invention provides a method comprising receiving sterilization process information from a sterilization facility via a computer network, generating a cost report based on the received information, and providing a network client with access to the report via the computer network.

In a further embodiment, the invention provides a system comprising a client computer and a network server. The client computer, associated with a sterilization facility, transmits sterilization process information via a computer network. The network server receives the sterilization process information from the client computer via the computer network, generates a cost report based on the received information, and provides a network client with access to the report via the computer network.

The invention is capable of providing one or more advantages. In general, the invention can promote the delivery of effective sterilization services. In some embodiments, the invention can improve workflow, inventory control, accounting, record-keeping, and/or compliance with applicable standards. With the invention, sterilization personnel can obtain ready access to information concerning sterilization procedures and control of parameters necessary for proper sterilization.

Automated distribution of materials used in sterilization procedures can provide more efficient inventory management and ensure availability of vital materials, including consumable materials and electronic information used in sterilization processes. Also, use of automated purchasing systems can simplify the ordering of materials by sterilization facility personnel. In addition, with the invention, a sterilization facility can benefit from automation and centralization of process tracking and cost accounting. The invention also can facilitate reporting to regulatory agencies and independent audit organizations.

As a further advantage, the network server may use the same sterilization process information provided by a sterilization facility for multiple purposes in some embodiments. For example, the network server may prepare sterilization process reports based on the sterilization process information, and extract information to determine usage levels for materials and equipment. In this manner, the network server can also estimate inventory levels, order additional materials based on the inventory levels, and schedule maintenance of sterilization equipment.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
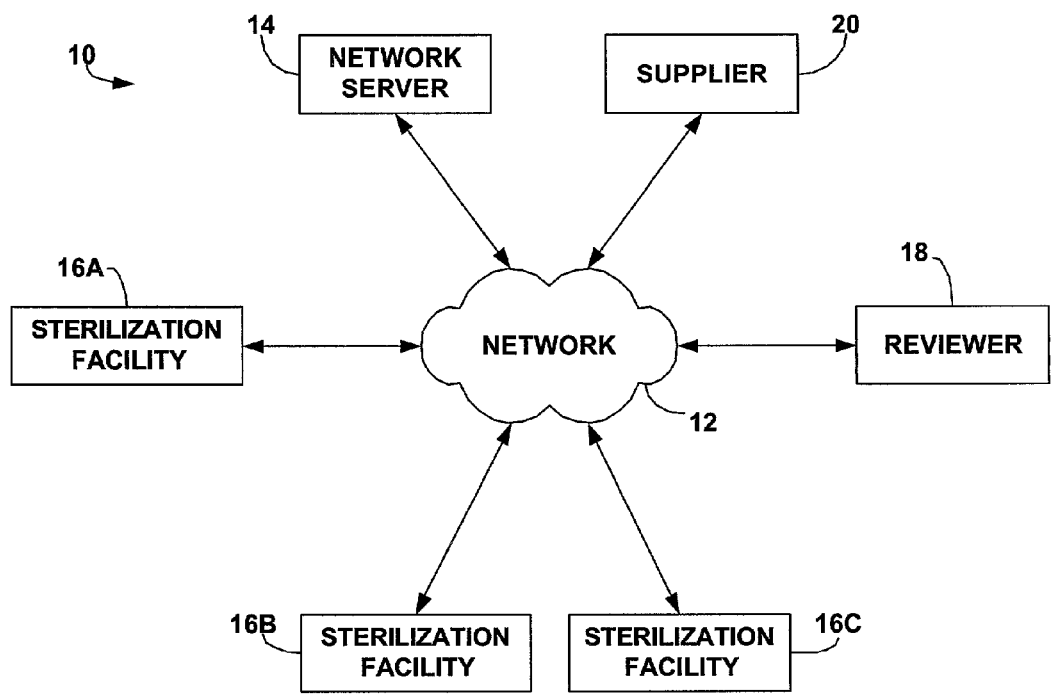
FIG. 1 is a block diagram illustrating an example system for managing information and material distribution for sterilization facilities via a computer network.

FIG. 1 is a block diagram illustrating a system 10 for management of information and distribution of materials for sterilization facilities. System 10 is implemented via a computer network 12, which may take the form of a local area network, wide area network, or a global computer network such as the World Wide Web. As shown in FIG. 1, system 10 may include a network server 14 coupled via network 12 to a number of client computers associated with sterilization facilities 16A, 16B, 16C, reviewer 18 and supplier 20. Network server 14 provides sterilization facilities 16 with access to information relating to sterilization processing. In addition, network server 14 receives sterilization process information from sterilization facilities 16.

In general, network server 14 operates as a central management server for one or more of sterilization facilities 16. Network server 14 may include one or more computers that cooperate to provide the functionality described herein. In addition, network server 14 may execute a variety of software applications that interact with software processes running on different machines to provide the functionality described herein. As will be described, network server 14 can be used to promote delivery of effective sterilization services by sterilization facilities 16. In particular, network server 14 can improve workflow, inventory control, recordkeeping and compliance with applicable standards. For example, sterilization facilities 16 can access network server 14 to obtain detailed technical information concerning sterilization procedures, products and equipment. Based on information provided by sterilization facilities 16, network server 14 can trigger distribution of sterilization materials from supplier 20 to the sterilization facilities, promoting efficient inventory management and availability of materials. In addition, network server 14 can provide sterilization process tracking and automatically generate compliance reports for inspection by reviewer 18.

Sterilization facilities 16 and reviewer 18 are network clients within system 10. Each sterilization facility 16 may take the form of a health care facility, such as a hospital or clinic, or a department within a health care facility such as central services, infection control, an operating room, a laboratory, or an accounting department that perform, manage or make use of sterilization services. Reviewer 18 may take the form of a regulatory agency or an independent audit organization responsible for verifying compliance of sterilization facilities 16 with applicable standards. In addition, reviewer 18 may be part of an organization internal to a health care facility. Supplier 20 may take the form of a manufacturer or distributor of sterilization materials, such as sterilizer equipment, sterilants, pack lists, indicators and the like. System 10 may have numerous sterilization facilities 16, reviewers 18 and suppliers 20, each of which may interact with network server 14 via network 12.

The client computers associated with sterilization facilities 16, reviewer 18 and supplier 20 may take the form of a variety of devices that permit a user to access resources on network 12. Examples of suitable client computers include desktop or portable computers operating in a Windows, Macintosh, Unix, or Linux environment, personal digital assistants (PDA's), based on the Palm, Windows CE, or similar operating system environments, Internet-equipped wireless telephones, and other Internet appliances. Each client computer may execute a graphical viewing application, such as a web browser, to access resources residing on network server 14 or other network resources.

Network server 14 may generate web pages, e.g., encoded with Hypertext Markup Language (HTML), Extensible Markup Language (XML), or the like, and may incorporate tags that point to objects or files stored on other network resources. When product information is requested, for example, network server 14 may embed tags for objects or files stored at supplier 20, or simply redirect sterilization facility 16 to a web site maintained by supplier 20. Thus, the content of web pages assembled for sterilization facilities 16 may include objects obtained from a variety of resources within network 12. In some embodiments, network server 14 and supplier 20 maybe integrated with one another. In the example of FIG. 1, however, network server 14 and supplier 20 are separate entities and maintain separate servers on network 12.

Figure 2:
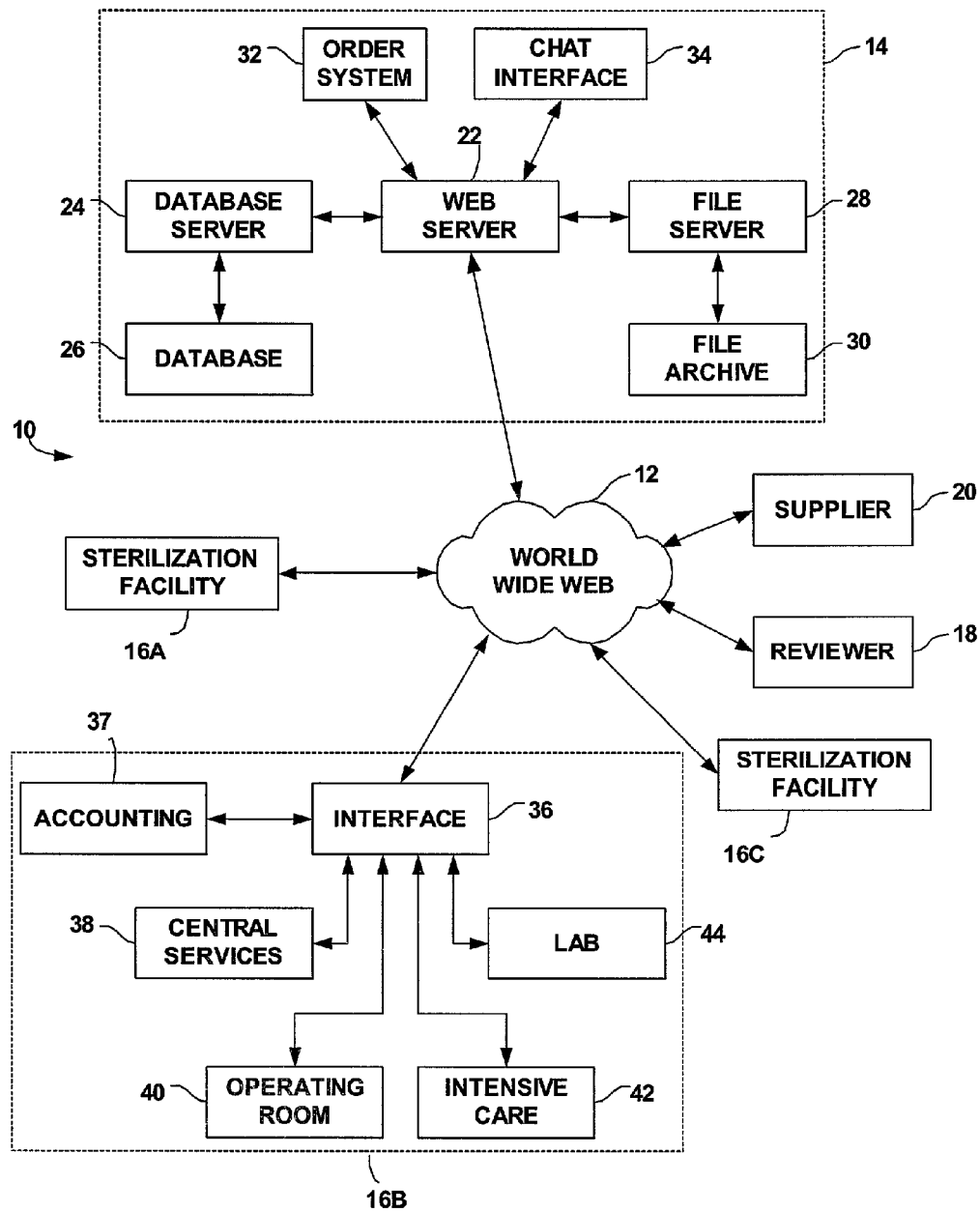
FIG. 2 is a block diagram illustrating the system of FIG. 1 in greater detail.

FIG. 2 is a block diagram illustrating system 10 of FIG. 1 in greater detail. As shown in FIG. 2, network 12 may be implemented via the World Wide Web. Also, network server 14 may include a collection of computers, including a web server 22, database server 24, and file server 28, that interact with database 26 and file archive 30. Web server 22 interacts with database server 24 to identify objects and files to be served with web pages. The locations of the objects and files are indicated within database 26. Web server 22 interacts with file server 28 to access the objects and files identified by database 26 within file archive 30. Web server 22 also may interact with an order system 32 and a chat interface 34. Order system 32 permits web server 22 to generate orders for delivery of sterilization materials to particular sterilization facilities 16.

Chat interface 34 manages interactive communications between personnel associated with sterilization facilities 16 and technical experts in the field of sterilization, as well as other sterilization personnel associated with different sterilization facilities. In this manner, sterilization personnel can submit questions to experts and share experiences with both experts and other sterilization personnel across a broad geographic community. This form of interactive communication may relate to use of sterilization products already purchased by sterilization facilities 16, or prospective products that a sterilization facility is considering for use in its operations. In addition, in some embodiments, supplier 20 may use the chat interface 34, email or other communication media to provide sterilization facilities 16 with notices concerning new products, documentation for existing products, and advice about the suitability of new materials for sterilization processes used by a particular sterilization facility. In this sense, the communication from experts or manufacturers may be personalized.

As further shown in FIG. 2, sterilization facility 16B may provide an interface 36 to network 12 for access by personnel associated with a number of departments within a health care facility. For example, sterilization facility 16B may include independent sterilization facilities associated with accounting 37, central services 38, operating room 40, intensive care 42, and various medical laboratories 44, as well as other departments such as receiving, maintenance and procedure scheduling. Each independent sterilization facility 37, 38, 40, 42, 44 may have one or more client computers that communicate with interface 36 via an intranet or other local area network. In this case, interface 36 acts as an intranet server that submits and receives information via web 12 on behalf of the independent sterilization facilities 37, 38, 40, 42, 44. Other sterilization facilities 16A, 16C may be associated with only a single department that communicates directly via network 12.

A firewall preferably is provided as a security measure. The firewall separates database server 24 and file server 28 from network server 14 to avoid unauthorized intrusions into the information maintained for particular sterilization facilities 16. Due to its nature as a repository of information concerning sterilization processing of individual sterilization facilities 16 and health care organizations, the security and confidentiality of database 26 and file archive 30 is a serious concern. To promote increased security and confidentiality of the information, web pages generated by network server 14 can be communicated using public key encryption mechanisms such as SSL. Other security measures, such as the use of login accounts for network clients, can provide added benefits.

Figure 3:
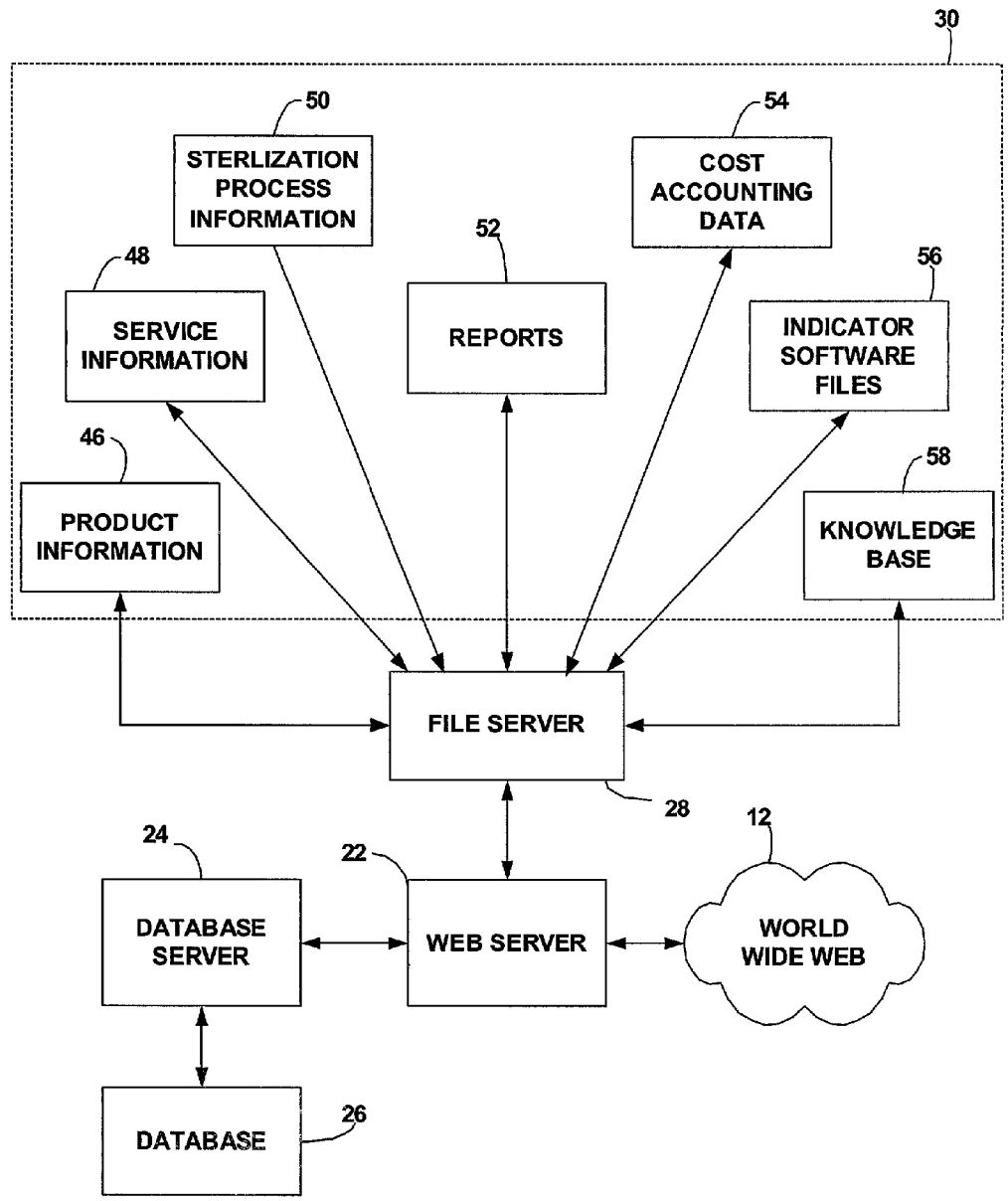
FIG. 3 is a block diagram illustrating an example file archive associated with a network server of FIG. 1.

FIG. 3 is a block diagram illustrating a file archive 30 associated with network server 14. As shown in FIG. 3, file archive 30 may store a variety of personalized information about particular sterilization facilities 16. In this manner, network server 14 can process and deliver information on a customized basis for an individual sterilization facility 16. To that end, file archive 30 may include files containing product information 46 that pertains to a particular sterilization facility 16.

The files may contain catalog information identifying products, product capabilities and characteristics, pricing, and the like. In some cases, the files may define links to other network resources or objects or files stored on other resources. For example, a product information file served by network server 14 may be a web page with tagged objects obtained from a server associated with supplier 20. Alternatively, a sterilization facility 16 may be redirected to a server associated with supplier 20 to obtain detailed product information.

Database server 24 may identify the product information files or other files pertaining to the sterilization facility 16 by reference to a profile in database 26. The profile can be built for a sterilization facility 16 based on the individual characteristics of its operations, such as the particular types of equipment, sterilants, pack lists and indicators the facility uses in sterilization processing, the size of the facility, and the throughput and product consumption of the facility. Different sterilization facilities 16 may have different profiles, reflected in database 26, which identify different sets of product information 46.

Hence, different sets of files may be organized within file archive 30 for particular sterilization facilities 16 by directory mapping. More preferably, however, a profile in database 26 maps various files within file archive 30 to particular sterilization facilities 16. In other words, the profile can be used by web server 22 to select, for individual sterilization facilities 16, subsets of the information provided in file archive 30. Based on the profile, a sterilization facility 16 is permitted to gain network access to selected subsets of the larger body of information. In this manner, information for one individual sterilization facility 16A can be protected from view by the other sterilization facilities 16B, 16C. The profile may be built initially based on an online or offline survey taken by the sterilization facility 16, and refined over time by interaction with the sterilization facility.

File archive 30 may have other types of information that can be arranged for or mapped to a particular sterilization facility 16 on a customized basis. For example, file archive 30 may store service information 48, which indicates the type of maintenance services required by a sterilization facility 16 based on the installed based of sterilization equipment. Service information 48 may indicate a schedule for maintenance of such equipment, and may be accessed by not only sterilization facility 16 but also by service personnel who contract with sterilization facility for maintenance services. In this case, service information 48 may be formatted for automated use with scheduling software used by service personnel.

Service information 48 may be based on a static, time-based metric for scheduling maintenance of sterilizer equipment. For example, maintenance can be scheduled on a monthly or quarterly basis. Alternatively, network server 14 may schedule maintenance based on sterilization process information 50 received from sterilization facilities 16 that indicates actual usage of equipment. Sterilization process information 50 can be stored in file archive 30 and used to dispatch service personnel, trigger distribution of sterilization materials, and prepare sterilization process reports, as will be described. Maintenance services may be integrated with the services provided by network server 14 and the operations of supplier 20. Sterilization process information 50 may include specific data concerning sterilization processes and loads run through sterilization equipment at a sterilization facility over a period of time. Sterilization facility 16 may upload data representative of actual usage to web server 22 on a periodic basis, e.g., once per day.

Based on the data provided by sterilization facility 16, network server 14 can determine not only a maintenance schedule, but also an estimate of consumption of sterilization materials in the course of performance of the sterilization processes. By estimating consumption, network server 14 can anticipate a need for additional sterilization materials by the particular sterilization facility 16. Network server 14 can track history and usage patterns of particular types of sterilization materials. On this basis, network server 14 can trigger distribution of additional sterilization materials to sterilization facility 16 on a predictive basis, ensuring ready availability of the sterilization materials on an automated basis without the need for significant human intervention.

Network server 14 may generate a request for particular sterilization materials, for example, and communicate the request to an order system 32, as shown in FIG. 2, or directly to a supplier 20 via network 12. Order system 32 passes the request along to a supplier 20. In each case, supplier 20 responds by shipping the sterilization materials to the particular sterilization facility 16. Electronic payment can be readily arranged between sterilization facility 16 and supplier 20. In some embodiments, network server 14 may be operated by a supplier 20 such that the services offered by the network server are integrated with the operations of the supplier.

In some embodiments, network server 14 may communicate an email, page or other message to personnel associated with a sterilization facility 16 prior to requesting distribution of materials. The message may take the form of a simple reminder that the inventory of particular sterilization materials may require replenishment. In this, case, the sterilization facility personnel may contact the supplier to order additional sterilization materials. Alternatively, the message may provide an interactive medium such as a hypertext link that can be used to acknowledge approval of a proposed order of sterilization materials. For example, the message may list the details of a purchase order and an "approval" button. When a sterilization facility personnel clicks on the button, web server 22 receives notification of approval and proceeds with the order on an automated basis, as described above. In any event, sterilization facility 16 benefits from automated monitoring of its inventory based on analysis of sterilization process information 50 uploaded to web server 22 from the sterilization facility.

Network server 14 may use sterilization process information 50 to prepare not only orders for sterilization material, but also reports 52 that track the sterilization operations of a sterilization facility 16 over a period of time. Reports 52 may contain information relating to the use of particular sterilization equipment, process parameters, particular loads processed, and particular packs within a load. This type of report 52 can be used to record the precise conditions and characteristics associated with the actual sterilization processing operations performed by a sterilization facility. In this manner, a reviewer 18, e.g., a regulatory agency or independent audit organization, can use the report to verify compliance with applicable standards. In some cases, a report 52 may integrate sterilization processing information received from two or more sterilization facilities 16, e.g., if the sterilization facilities are controlled by a common entity such as a hospital, clinic, or health maintenance organization. Report 52 also can be made accessible to personnel within a health care facility, e.g., for internal auditing or analysis.

In each case, report 52 provides automated, centralized record-keeping that eases the administrative burden on individual sterilization facilities 16. In addition, reviewer 18 can readily access reports 52 online, either by accessing network server 14 or receiving emails with attachment documents containing report content. In some embodiments, reviewer 18 may download a plug-in from network server 14 that permits viewing of information embodied in reports 52, e.g., graphically. In other embodiments, network server 14 may be configured to assemble a report 52 for reviewer 18 only upon request. In this case, network server 14 may assemble items stored in sterilization process information 50 for a particular sterilization facility 16. Also, a sterilization facility 16 may be permitted to control access to reports 52 by reviewers 18, including the scope of access and the time at which the reviewer can access the reports. For example, in some embodiments, sterilization facility 16 may limit access by reviewers 18 to only those portions of an overall report 52 necessary for evaluation of compliance.

As an example, reviewer 18 may be an independent audit organization such as the Joint Commission on Accreditation of Healthcare Organizations (JCAHO). The audit organization, as reviewer 18, retrieves sterilization process reports from network server 14, and reviews the reports for compliance with applicable standards. The online availability of the reports can greatly reduce the administrative overhead required by a sterilization facility 16 when an audit takes place. In addition, in the event of a recall, the necessary data concerning which instruments were affected and the sterilization processing status of each pack can be readily retrieved for tracking purposes.

To facilitate preparation of a report 52, sterilization process information 50 uploaded by sterilization facility 16 should include sufficient data concerning sterilization processes carried out by the sterilization facility. For a sterilization load using biological indicators, for example, a sterilization facility 16 may provide a sterilization summary including the date a load is processed, the particular sterilizer used, e.g., by number or name, the type of sterilizer, the start and end times for a load, a load identification, an indication of indicator growth, i.e., positive or negative, and a status indication, i.e., whether the load was released or is in process. For a chemical indicator, the sterilization facility would include similar information plus a simple indication of whether the chemical indication exhibited a pass or fail status. The sterilization summary also may include process parameters such as cycle time, sterilization time, temperature, pressure, humidity, sterilant concentration and the like.

Network server 14 also may use sterilization process information 50 to assemble cost-accounting data 54 for a sterilization facility. Sterilization process information 50 may identify sterilization processing operations associated with departments or other entities within a health care facility. Using sterilization process information 50 and a cost database prepared for a sterilization facility 16, network server 14 can prepare cost accounting data 54, which then facilitates cost management and charge-backs to appropriate departments. The cost account data can be made available for online access and downloading by accounting personnel associated with a sterilization facility 16. Alternatively, network server 14 may forward the cost account data to sterilization facility 16 on a periodic basis, e.g. monthly.

With further reference to FIG. 3, file archive 30 also may store indicator software files 56 that are used to drive a printer to produce chemical indicators. As one option, a downloadable catalog of standardized sterilization pack software can be displayed in a web page delivered to a sterilization facility 16 by network server 14. The sterilization facility personnel can then choose the desired sterilization pack, and download the associated software. Each indicator software file 56 may define a bar code, alphanumeric code, or other code that carries information sufficient to identify a particular sterilization pack and the sterilization conditions under which it is processed. Thus, indicator software file 56 could be an executable file that functions as a custom print driver to produce an indicator, or simply a graphic file that defines a bar code or other code for printing via standard print drivers.

In some cases, the indicators may be printed with self-indicating ink that changes appearance to indicate exposure to sufficient sterilization conditions. If self-indicating ink is used, it may be shipped to sterilization facility 16 in response to a request by network server 14 for "print-on-demand" applications. The bar codes, in turn, can be used within a sterilization facility 16 to track individual sterilization packs and sterilization conditions. The information contained in the bar code, upon scanning, could form part of the sterilization process information uploaded from a sterilization facility 16 to network server 14 for other purposes as described above.

Chemical indicators may be pre-printed by a manufacturer according to sterilization process information uploaded to network server 14 by a sterilization facility 16, and then shipped to the sterilization facility. In addition, sterilization facilities 16 can order settings for specific types and cycles of sterilization as they install new equipment or begin to use new types of sterilization cycles, e.g., longer steam cycles and the like. Similar techniques, relying on information uploaded by sterilization facilities 16, could be used to obtain biological indicators, sterilization tape and other types of sterilization indicators.

File archive 30 also may include a set of files that form a knowledge base 58. Knowledge base 58 may store technical reports, advisories, user documentation and other information associated with sterilizer equipment, processes, and materials. In addition, knowledge base 58 may store protocols and process parameter tables useful to personnel associated with sterilization facilities 16 in processing particular types of sterilization loads. Case histories, trouble-shooting tips, problem fixes, and transcripts from interactive chat sessions with sterilization experts and online education seminars can also be provided in knowledge base 58.

If desired, profiles can be applied to filter portions of file archive 30 from view by sterilization facilities 16. If a sterilization facility 16 uses only steam-based sterilizers, for example, there may be no need to access information in knowledge base 58 pertaining to ethylene oxide sterilization. Accordingly, database 26 may map particular files in knowledge base 58 for access by particular sterilization facilities 16. Alternatively, database 26 may flag particular files to prohibit access by particular sterilization facilities 16. This type of access scheme also can be made applicable to reviewers 18 to limit the scope of access.

In some embodiments, system 10 may be used to accumulate information concerning best practices and trends in sterilization processing from multiple network clients. This feature may be particularly useful for organizations responsible for management of multiple sterilization facilities 16. For example, a health maintenance organization that manages several different hospitals may be given access to sterilization process information collected from those hospitals. The information, which may include types of sterilization processes used, consumption of sterilization materials, throughput, process control settings and the like within the individual hospitals, can be used to develop overall trends and establish best practices for sterilization processing.

The larger management organization can use the information to make purchasing decisions, schedule preventative maintenance, perform trouble shooting of problems, develop training programs, improve process quality and throughput, and minimize recalls. Thus, network server 14 can be configured to accumulate information for trend analysis and establishment of best practices guidelines and provide network clients with access to such information. Network server 14 also may provide more general best practices information obtained from industry organizations such as the Association for the Advancement of Medical Instrumentation (AAMI), the Association of Perioperative Registered Nurses (AORN), the American Society for Healthcare Central Service Professionals (ASHCSP), and others, and provide frequent updates.

The trend analysis and best practices guidelines may be processed by the network client based on the information form network server 14, and then uploaded, if desired, to the network server for access by other network clients. Alternatively, network server 14 may simply store the raw information used by individual network clients in trend analysis and establishment of best practices. Typically, access to information pertaining to a group of sterilization facilities 16 will be limited to network clients affiliated with those facilities rather than shared with others.

If information is gathered from a relatively large number of health care facilities, the trend information can be used to compare any given hospital to a standard or "norm." Health care facilities, such as hospitals, typically are quite competitive, with each hospital seeking to distinguish itself in the quality and level of service it provides. Trend information could be used to provide a relative ranking of a hospital in the field of sterilization services, and reveal areas for improvement.

Figure 4:
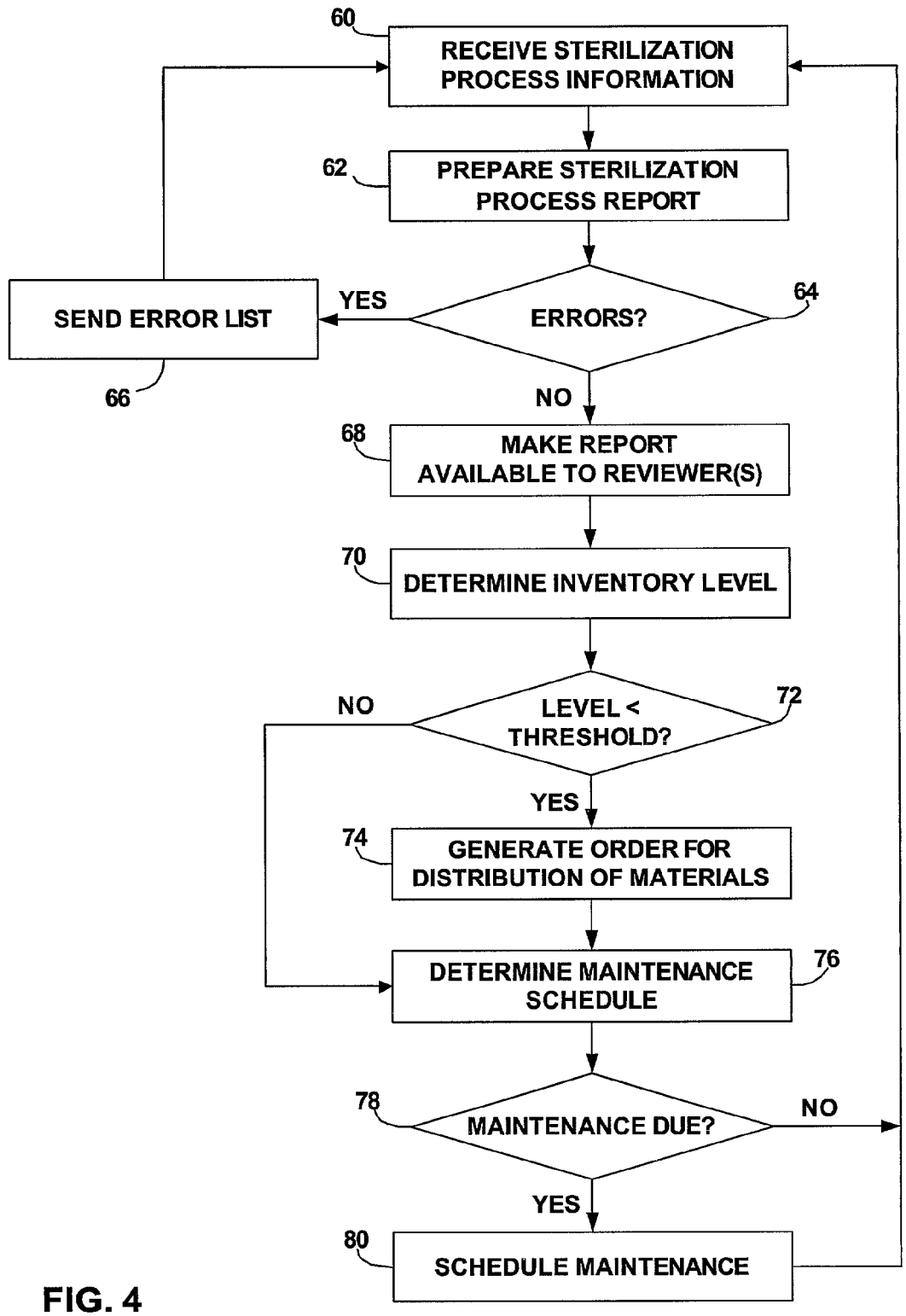
FIG. 4 is a flow chart illustrating generation of reports and distribution of sterilization materials in the system of FIG. 1.

FIG. 4 is a flow chart illustrating generation of reports and distribution of sterilization materials in system 10 of FIG. 1. As shown in FIG. 4, upon receipt of sterilization process information (60) from a sterilization facility 16 via network 12, network server 14 prepares a sterilization process report (62) for access by the sterilization facilities and reviewer 18. In some embodiments, network server 14 may apply an error checking process (64) to identify errors within the sterilization process information. Errors may arise due to human error in entry of the sterilization process information. If errors exist, network server 14 may generate an error list and send it to the pertinent sterilization facility (66). If not, network server 14 makes the report available to authorized reviewers 18 via network 12 (68).

Network server 14 also may analyze the sterilization process information to determine inventory levels of sterilization materials (70) for the pertinent sterilization facility 16. If the inventory level drops below a predetermined threshold (72), network server 14 may generate an order for distribution of additional sterilization materials to the sterilization facility (74). If the inventory level is satisfactory (no branch from 72), or upon generation of an order for additional sterilization materials, network server 14 may further analyze sterilization process information to determine a maintenance schedule for the sterilization equipment used by the sterilization facility 16 (76). In particular, based on the number and types of sterilization loads processed by sterilization facility 16, network server 14 determines whether equipment maintenance is due (78). If maintenance is due, network server 14 issues an order for scheduling of maintenance (80). In some cases, the order may be directed to a particular individual for immediate sterilizer maintenance. If no maintenance is due, network server 14 waits for the next set of sterilization process information to be uploaded (no branch of 80).

As discussed above, network server 14 may analyze the sterilization process information to estimate consumption of sterilization materials, as well as usage of sterilization equipment. Thus, in some embodiments, network server 14 may use the same sterilization process information for multiple purposes, e.g., to prepare sterilization process reports, estimate inventory levels, and schedule sterilizer equipment maintenance.

Figure 5:
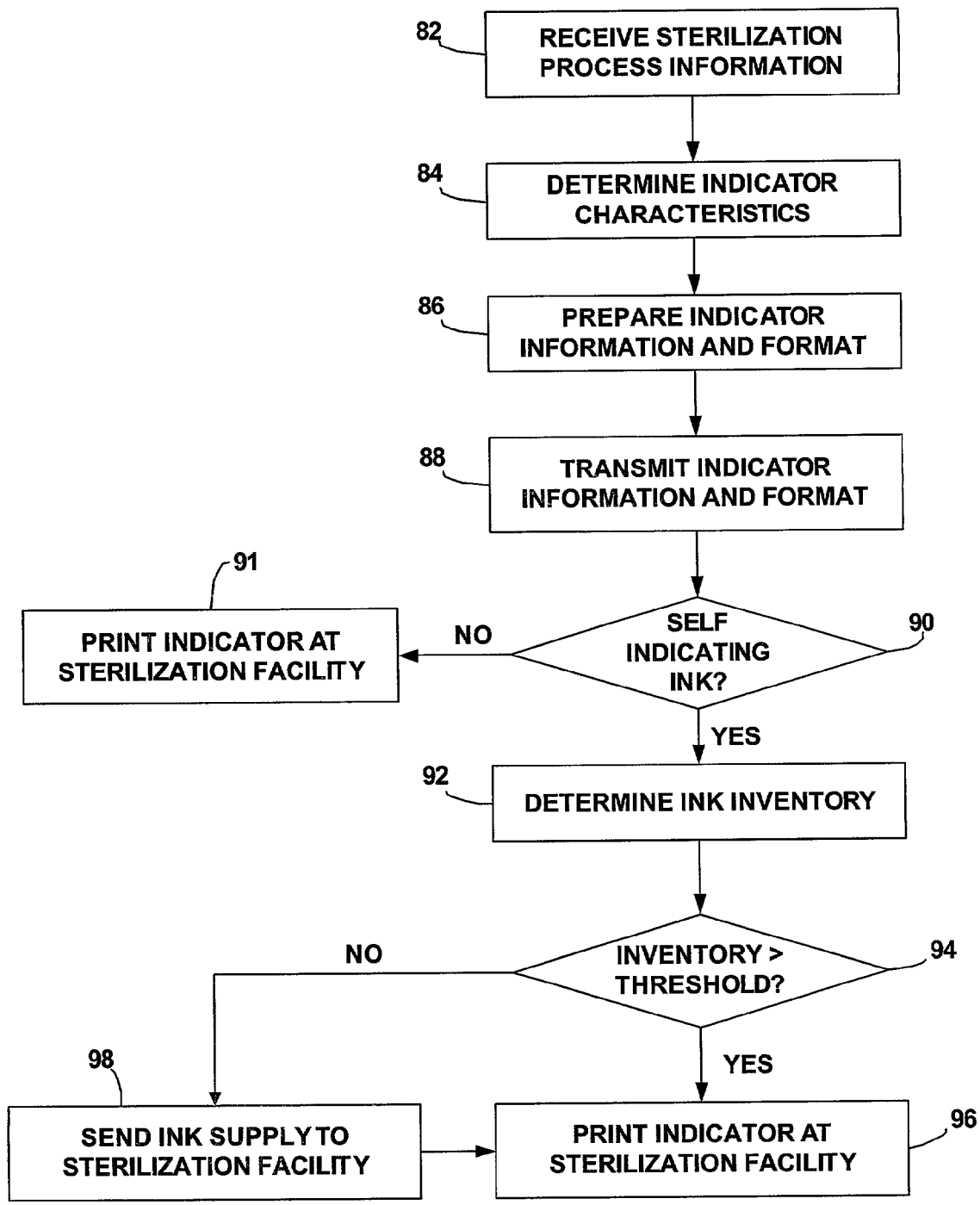
FIG. 5 is a flow chart further illustrating distribution of sterilization materials in the system of FIG. 1.

FIG. 5 is a flow chart further illustrating distribution of sterilization materials in the system of FIG. 1. In particular, FIG. 5 illustrates the distribution of indicator materials. As shown in FIG. 5, upon receipt of sterilization process information (82), network server 14 may determine the characteristics of indicators (84) used in one or more of the sterilization processes performed by sterilization facility 16. Based on this determination, if inventories of the indicator are running for a print on demand application, network server 14 prepares indicator information and formats it appropriately (86). Network server 14 then transmits the indicator information and format to sterilization facility 16 (88).

If self-indicating ink is required (90) by sterilization facility 16, rather than ordinary ink, network server 14 may assess the inventory of self-indicating ink maintained by the sterilization facility (92). If self-indicating ink is not required, the indicator is simply printed at sterilization facility 16 (91). If the inventory of ink is greater than a predetermined threshold (94), sterilization facility 16 may proceed to print the indicator (96) defined by the indicator information and format sent by network server 14. If the inventory is less than the predetermined threshold (94), indicating insufficient supply, network server 14 prepares an order to send an additional supply of ink to the sterilization facility (98).

Various embodiments of the invention have been described. These and other embodiments are within the scope of the following claims.

What is claimed is:

1. A method comprising:
   receiving sterilization process information from a sterilization facility via a computer network, wherein the sterilization process information includes characteristics of a sterilization process;
   identifying a type of a sterilization material based on the characteristics of the sterilization process;
   determining consumption of a quantity of the sterilization material by the sterilization facility based on the sterilization process information; and
   processing an order for delivery of an additional quantity of the sterilization material to the sterilization facility based on the determination.

2. The method of claim 1, wherein the sterilization material includes at least one of sterilant, pack material, and indicators.

3. The method of claim 1, wherein the sterilization material includes electronic information for generation of a printed indicator, the method further comprising transmitting the electronic information to the client via the computer network.

4. The method of claim 1, wherein the sterilization material includes self-indicating ink, the method further comprising delivering a quantity of the ink to a client.

5. A system comprising:
   a client computer, associated with a sterilization facility, that transmits sterilization process information via a computer network, the sterilization process information including characteristics of a sterilization process; and
   a network server that receives the sterilization process information from the client computer via the computer network, identifies a type of a sterilization material based on the characteristics of the sterilization process, determines consumption of a quantity of the sterilization material by the sterilization facility based on the sterilization process information, and processes an order for delivery of an additional quantity of the sterilization material to the sterilization facility based on the determination.

6. The system of claim 5, wherein the sterilization material includes at least one of sterilant, pack material, and indicators.

7. The system of claim 5, wherein the sterilization material includes electronic information for generation of a printed indicator, and the network server transmits the electronic information to the client via the computer network.

8. The system of claim 5, wherein the sterilization material includes self-indicating ink, and the network server processes an order for delivery of a quantity of the ink to the client.

9. A method comprising:
   receiving sterilization process information from a sterilization facility via a computer network, wherein the sterilization process information includes characteristics of a sterilization process;
   identifying a type of a sterilization material based on the characteristics of the sterilization process;
   determining consumption of a quantity of the sterilization material by the sterilization facility based on the sterilization process information;
   processing an order for delivery of an additional quantity of the sterilization material to the sterilization facility based on the determination;
   scheduling maintenance for sterilization equipment associated with the sterilization facility based on the sterilization process information;
   generating a report that indicates compliance with sterilization process standards based on the sterilization process information; and
   providing a reviewer with access to the report via the computer network.

10. The method of claim 9, wherein the reviewer is a regulatory agency or an audit organization.

11. The method of claim 9, wherein the report identifies individual sterilization loads and load contents, and the report includes sterilization processing characteristics for the individual sterilization loads, the sterilization processing characteristics for each load including type of sterilizer, sterilizer identification, cycle time, sterilization time, temperature, and pressure.

12. A system comprising:
    a client computer, associated with a sterilization facility, that transmits sterilization process information via a computer network, the sterilization process information including characteristics of a sterilization process; and
    a network server that:
       identifies a type of a sterilization material based on the characteristics of the sterilization process,
       determines consumption of a quantity of the sterilization material by the sterilization facility based on the sterilization process information;
       processes an order for delivery of an additional quantity of the sterilization material to the sterilization facility based on the determination;
       schedules maintenance for sterilization equipment associated with the sterilization facility based on the sterilization process information;
       generates a report that indicates compliance with sterilization process standards based on the sterilization process information; and
       provides a reviewer with access to the report via the computer network.

13. The system of claim 12, wherein the reviewer is a regulatory agency or an audit organization.

14. The system of claim 12, wherein the report identifies individual sterilization loads and load contents, and the report includes sterilization processing characteristics for the individual sterilization loads, the sterilization processing characteristics for each load including type of sterilizer, sterilizer identification, cycle time, sterilization time, temperature, and pressure.

* * * * *